(12) United States Patent
Rogers

(10) Patent No.: US 7,034,000 B2
(45) Date of Patent: Apr. 25, 2006

(54) PEPTIDES DERIVED FROM THE HUMAN AMYLOID PRECURSOR PROTEIN

(75) Inventor: Jack Rogers, Arlington, MA (US)

(73) Assignee: The Brigham and Women's Hospital, Inc., Boston, MA (US)

( * ) Notice: Subject to any disclaimer, the term of this patent is extended or adjusted under 35 U.S.C. 154(b) by 418 days.

(21) Appl. No.: 09/978,178

(22) Filed: Oct. 17, 2001

(65) Prior Publication Data

US 2003/0004101 A1    Jan. 2, 2003

Related U.S. Application Data

(60) Provisional application No. 60/243,403, filed on Oct. 27, 2000.

(51) Int. Cl.
*A61K 38/17* (2006.01)
*C07K 14/435* (2006.01)

(52) U.S. Cl. .......................... 514/13; 530/326
(58) Field of Classification Search ............... 514/12, 514/13; 530/326; 930/10
See application file for complete search history.

(56) References Cited

FOREIGN PATENT DOCUMENTS

WO    WO 99/58564    11/1999

OTHER PUBLICATIONS

Balla, et al., "Endothelial Cell Heme Oxygenase and Ferritin Induction in Rat Lung by Hemoglobin *in Vitro.*" *Am. J. Physiol.* 268:1.321-1.327 (1995).
Balla, et al., "Ferritin: A Cytoprotective Antioxidant Stratagem of Endothelium." *J Biol Chem* 267:18148-18153.
Bowes, et al., "Reduction of Neurological Damage by a Peptide Segment of the Amyloid β A4 Protein Precursor in a Rabbit Spinal Cord Ischemia Model." *Exper. Neurol.* 129:112-119 (1994).
Dávalos, et al., "Body Iron Stores and Early Neurologic Deterioration in Acute Cerebral Infarction." *Neurology* 54: 1568-1574 (2000).
de Silva, et al., "Purification and Characterization of Fet3 Protein, a Yeast Homologue of Ceruloplasmin." *J. Biol. Chem.* 272:14208-14213 (1997).
Juckett, et al., "Ferritin Protects Endothelial Cells from Oxidized Low Density Lipoprotein *in Vitro.*" *Am. J Pathol.* 147:782-789 (1995).
Kang, et al., "The Precursor of Alzheimer's Disease Amyloid A4 Protein Resembles a Cell-Surface Receptor." *Nature* 325:733-736 (1987).
Lawson, et al., "Solving the Structure of Human H Ferritin by Genetically Engineering Intermolecular Crystal Contacts." *Nature* 349:541-544 (1991).
Jin, et al., "Peptides Containing the RERMS Sequence of Amyloid β/A4 Protein Precursor Bind Cell Surface and Promote Neurite Extension." *J. Neurosci.* 14:5461-5470 (1994).
Rogers, et al., "Iron Oxidation and Neuroprotection by Secreted Amyloid Precursor Protein." *Soc. for Neurosci. Abstracts* 27:27 (2001).
Yamamoto, et al., "The Survival of Rat Cerebral Cortical Neurons in the Presence of Trophic APP Peptides." *J. Neurobiology* 25:585-594 (1994).

*Primary Examiner*—Robert C. Hayes
(74) *Attorney, Agent, or Firm*—Michael A. Sanzo; Fitch, Even, Tabin & Flannery

(57) ABSTRACT

The present invention is directed to certain peptides that correspond to sequence elements within the human Alzheimer's amyloid precursor protein (APP). These peptides may be used to protect cells from iron catalyzed oxidative damage.

15 Claims, 1 Drawing Sheet

US 7,034,000 B2

PEPTIDES DERIVED FROM THE HUMAN AMYLOID PRECURSOR PROTEIN

CROSS REFERENCE TO RELATED APPLICATION

The present application claims the benefit of U.S. provisional application No. 60/243,403, filed on Oct. 27, 2000 (now abandoned).

STATEMENT OF GOVERNMENT SUPPORT

The work leading to this invention was supported by one or more grants from the U.S. Government. The U.S. Government therefore has certain rights in the invention.

FIELD OF THE INVENTION

The present invention is directed to peptides derived from portions of the human amyloid precursor protein (APP) that have been found to protect cells from iron-catalyzed oxidative damage.

BACKGROUND OF THE INVENTION

The human APP protein has been isolated and fully characterized (Kang, et al., *Nature* 325:733–436 (1987), designated hereinafter as "APP-695")). This protein contains a segment (the "RERMS" domain) that protects neurons from injury associated with ischemia and that promotes neuronal growth (Bowes, et al., *Exp. Neurol.* 129:112–119 (1994)). The present invention is based upon the discovery that certain regions within APP, distinct from the RERMS domain, are also cytoprotective. These regions were identified based upon their homology to the iron oxidase domain of ferritin.

The H-ferritin iron oxidase domain is believed to protect vascular endothelial cells from damage caused by iron-catalyzed production of toxic hydroxyl radicals (Balla, et. al., *J. Biol. Chem.* 267:18148–18153 (1992); Juckett, et al., *Am. J. Pathol.* 147:782–789 (1995); Balla, et al., *Am. J. Physiol.* 268:321–327 (1995)). Mutations at specific sites in the ferritin heavy chain (particularly those affecting Glu63 and His66) result in a loss of oxidase activity and render the protein completely ineffective as a cytoprotectant (Lawson, et al., *Nature* 349:544 (1991)); Balla, et al., *Am. J. Physiol.* 268:L321–327 (1995)). It has been suggested that ferritin provides a locally trophic environment, promoting cellular growth in the vicinity of iron-catalyzed oxidative damage (Terada, et al., *Iron and Human Disease*, R. Lauffer, ed., pp. 313–329 (1992)). Proteins and peptides homologous to the iron oxidase domain of ferritin would be expected to have a similar effect and to be useful in preventing oxidative damage associated with reperfusion subsequent to a stroke or heart attack (Davalos, et al., *Neurology* 54:1568–1574 (2000)).

SUMMARY OF THE INVENTION

The present invention is based upon the discovery of amino acid sequence segments in the Alzheimer's amyloid precursor protein which align with the known cytoprotective iron oxidase site (residues 57 to 72) in H-ferritin. The first of these segments has been designated as the "ferroxidase sequence homology domain" ("FOX-1") and includes residues 337 to 358 of APP-695. FOX-1 is downstream of the RERMS sequence of APP (residues 319–335 of APP-695), a region that is known to be cytoprotective but whose mechanism of action has not been established. In addition to FOX-1, a second region in APP, designated "FOX-2," has been found that has even greater homology to the ferritin iron oxidase site. This region is found between amino acids 250 and 273 in APP-695 and, like FOX-1, has ferroxidase activity when synthesized as a distinct peptide.

In its first aspect, the invention is directed to a peptide that is useful in protecting human cells from oxidative damage, particularly iron-catalyzed oxidative damage. The peptide is between 10 and 44 amino acids in length and contains the sequence REWEEAERQA (SEQ ID NO: 1). The peptide may also include from 1 to 14 additional amino acids lying immediately C-terminal to SEQ ID NO: 1 with the additional amino acids being in the order of the sequence: KNLPKADKKAVIQH (SEQ ID NO: 2). Thus, the first amino acid added C-terminal to the final A in SEQ ID NO: 1 would be K. The next amino acid would be N, etc. In addition to amino acids lying C-terminal to SEQ ID NO: 1, the peptide may include 1 to 20 amino acids lying immediately N-terminal to this sequence. These amino acids would be in the order: FQKAKERLEAKHRERMSQVM (SEQ ID NO: 3). Therefore, the amino acid added immediately N-terminal to the first amino acid in SEQ ID NO: 1 would be M. The next would be V, etc.

There are several peptides that are especially preferred. Among these is a peptide that consists of the first ten amino acids in the FOX-1 domain and has the sequence REWEEAERQA (SEQ ID NO: 1). A second preferred peptide is 13 amino acids in length, having three additional C-terminal residues: REWEEAERQAKNL (SEQ ID NO: 4). A third preferred peptide is 24 amino acids in length and constitutes the complete FOX-1 domain. This peptide has the sequence: REWEEAERQAKNLPKADKKAVIQH (SEQ ID NO: 5). A fourth preferred peptide, the "827 peptide," contains the first 13 N-terminal amino acids of FOX-1 fused to nine amino acids from the RERMS domain of APP-695. Its sequence is: HRERMSQVMREWEEAERQAKNL (SEQ ID NO: 6).

The invention also includes a peptide corresponding to the complete FOX-2 domain. This peptide is also useful in protecting human cells from oxidative damage and has the sequence: DGDEVEEEAEPYEEATERTTSIA (SEQ ID NO: 7).

The invention encompasses any of the peptides discussed above in a substantially pure form. As used herein, the term "substantially pure" means that a peptide has been separated from other accompanying biological components and constitutes at least 50% of the proteinacious material in a sample, with percentages of greater than 85% being preferred. Many means are available for assessing the purity of a peptide within a sample, including analysis by polyacrylamide gel electrophoresis, chromatography and analytical centrifugation.

The invention is also directed to antibodies made by a process involving the injection of any one of the peptides discussed above into an animal capable of antibody production. These antibodies may be either polyclonal or monoclonal. In the latter case, it is preferred that antibody be made by a process involving the injection of a pharmaceutically acceptable preparation into a mouse, followed by fusing mouse spleen cell with myeloma cells.

In another aspect, the invention is directed to a substantially pure polynucleotide consisting of a nucleotide sequence encoding any one of the peptides described above. This polynucleotide may be used as the coding region in a vector designed to express peptide. When used in this manner, the polynucleotide should be operably linked to a promoter. The vector may be used to transform host cells for the purpose of producing peptide.

The invention also includes pharmaceutical compositions in unit dose form which contain one or more of the peptides. The phrase "unit dosage form" means a single drug administration entity. By way of example, a single tablet, capsule, or vial would be a unit dosage form. Administration of the unit dosage form will result in the delivery of sufficient peptide to produce a therapeutic effect. The pharmaceutical compositions will typically contain one or more excipients and a pharmaceutically acceptable solvent. Solutions for parenteral injection are generally preferred but other compositions may also be used.

Pharmaceutical compositions containing peptides may be used in a method for reducing oxidation-related damage in a patient suffering from a stroke, heart attack, or spinal injury. In this method, the patient is administered a therapeutically effective amount of the composition, preferably by injection or infusion. A "therapeutically effective" amount is a dosage sufficient to significantly reduce oxidative damage. Although the exact amount administered will vary depending upon a variety of clinical conditions, a therapeutically effective dose will typically be between 0.01 and 10 mg of peptide administered daily. Very high concentrations of peptide may be used at sites where the risk of oxidative damage is particularly great, e.g., at heart tissue immediately after a heart attack. For localized delivery of this type, peptide may be continuously infused at a concentration of up to 10 μM or more. Administration should take place as soon as possible after an attack and should be maintained for at least 3 days. The compositions may also be administered at the same daily dosages prior to a patient undergoing surgery to reduce or prevent cellular injury resulting from oxidative stress. Administration will be particularly useful in patients undergoing surgery affecting cardiac or neural tissue. Ideally, administration should occur about 20 minutes prior to surgery and should be continued post-operatively for at least 3 days.

In addition, the invention encompasses a method of protecting cells from oxidation-related damage by exposing the cells to an effective amount of one or more of the peptides described above. Usually this will be accomplished using solutions containing peptide at a concentration of between 1 μg/ml. and 1 mg/ml. Preferably, the cells in this method will be smooth muscle cells, vascular endothelial cells, or neuronal cells.

BRIEF DESCRIPTION OF THE FIGURES

FIG. 1 shows a portion of the APP protein (SEQ ID NO:8) that includes the RERMS and domain (SEQ ID NO:9) and FOX-1 domain (SEQ ID NO:5). A2 (SEQ ID NO:10) and 827 (SEQ ID NO:6) are both peptides which encompass a portion of the RERMS sequence (SEQ ID NO:9). Also shown is the location of these peptides with respect to a KPI insertion site and a peptide designated as Aβ(SEQ ID NO:11).

DETAILED DESCRIPTION OF THE INVENTION

A. Cytoprotective Peptides

Figure 1:
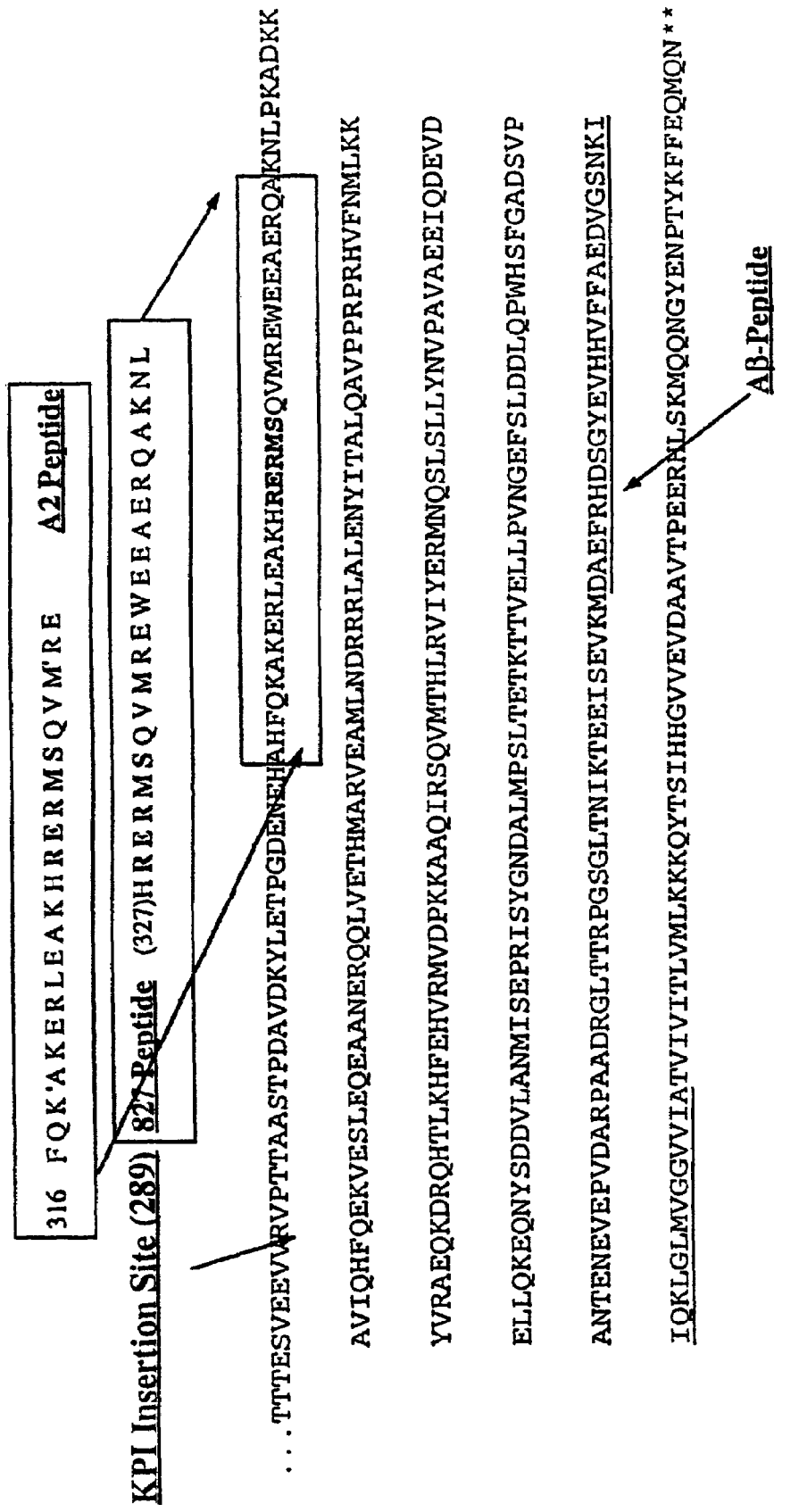
FIG. 1.

The present invention is directed to therapeutic peptides that display iron oxidase activity and that can be used to optimize conditions for nerve cell growth and regeneration after stroke, heart attack or spinal injury. The peptides all have sequences derived from regions within the APP-695 protein, with the most preferred peptides having sequences corresponding to SEQ ID NOs: 1-7. These peptides are relatively short in length and can be readily synthesized and purified using methods that are standard in the art of biochemistry.

It will be understood that the invention encompasses not only peptides that are identical to those described herein but also other peptides that are substantially the same in terms of structure and function. For example, it is often possible to substitute one or more amino acids in a protein or peptide without affecting its biological activity. Minor structural variations of this nature are encompassed by the invention provided that such variations do not substantially alter the cytoprotective characteristics of the peptide.

B. Polynucleotides Encoding Peptides

The invention also includes DNA sequences coding for the peptides described above. Based upon the amino acid sequences shown, polynucleotides may be synthesized with appropriate adaptors for insertion into a plasmid or phage vector. In order to express recombinant peptide, the vector should contain transcriptional and translational signals recognizable by an appropriate host cell and the peptide-coding sequence should be inserted in an operable linkage, i.e., it should be positioned so as to be under the control of the regulatory sequences found in the vector and in such a manner that mRNA is produced that is correctly translated into the peptide amino acid sequence.

Expression may take place in either eukaryotic or prokaryotic cells. Mammalian cells that can be used include, without limitation, NIH-3T3 cells, CHO cells, HeLa cells, LM(tk⁻) cells, etc. Vectors for each of these cell types are well-known in the art. Preferred eukaryotic promoters include those of the mouse metallothioneine I gene; the TK promoter of Herpes virus; the SV40 early promoter; and the CMV early promoter. Some of examples of prokaryotic promoters include those capable of recognizing T4 polymerases, the $P_R$ and $P_L$ promoters of bacteriophage lambda, and the trp, rec A, heat shock and lacZ promoters of *E. coli*. Expression vectors may be introduced into cells by methods such as calcium phosphate participation, microinjection, electroporation or viral transfer and cells expressing peptide can be selected using methods well-known in the art. One simple method for confirming the presence of peptide-encoding DNA in cells is to perform PCR amplification using primers selected based upon known sequences. In all cases standard methods for preparing and isolating DNA sequences may be used (see e.g., Sambrook et al.), *Molecular Cloning: A Laboratory Manual*, 2d. ed., Cold Spring Harbor Press (1989)).

Recombinant peptide may be purified using techniques well-known in the art. These may include filtration, precipitation, chromatography and electrophoretic methods. Purity can be assessed by performing electrophoresis on a polyacrylamide gel and visualizing peptide using standard staining techniques.

C. Antibodies

The present invention is also directed to antibodies made by a process involving injecting peptides into an appropriate animal. Methods for making and detecting antibodies are well-known to those of skill in the art as evidence by standard reference works such as: Harlow, et al., *Antibodies, A Laboratory Manual*, Cold Spring Harbor Laboratory, N.Y. (1988); Klein, *Immunology: The Science of Self-Nonself Discrimination*, (1982); Kennett et al., *Monoclonal Antibodies and Hydridomas: A New Dimension in Biological Analyses*, (1980); and Campbell, "Monoclonal Antibody and Technology," in: *Laboratory Techniques in Biochemistry and Molecular Biology*, (1984)).

"Antibody" as used herein, is meant to include intact molecules as well as fragments which retain their ability to bind antigen (e.g., Fab and F(ab')$_2$ fragments). These fragments are typically produce by proteolytically cleaving intact antibody using enzymes such as papain (to produce Fab fragments) or pepsin (to produce F(ab')$_2$ fragments). The term "antibody" also refers to both monoclonal antibodies and polyclonal antibodies. Polyclonal antibodies are derived from the sera of animals immunized with antigen. Monoclonal antibodies can be prepared using hybridoma technology (Kohler, et al., *Nature* 256:495 (1975); Hammerling, et al., in: *Monoclonal Antibody and T-Cell Hybridomas*, Elsevier, N.Y., pp. 563–681 (1981)). In general, this technology involves immunizing an animal, usually a mouse, with an intact protein or peptide. The splenocytes of the immunized animals are extracted and fused with suitable myeloma cells, e.g., SP$_2$O cells. After fusion, the resulting hybridoma cells are selectively maintained in HAT medium and then cloned by limiting dilution (Wands et al., *Gastroenterology* 80:225–232 (1981)). The cells obtained by such selection are then assayed to identify clones which secrete antibodies capable of binding to peptide.

The antibodies or fragments of antibodies of the present invention may be used to detect the presence of peptide in any of a variety of immunoassays. For example, antibodies may be used in radioimmunoassays or immunometric assays, also known as "two-site" or "sandwich" assays (See Chard, "An Introduction to Radiommune Assay and Related Techniques," in: *Laboratory Techniques in Biochemistry and Molecular Biology*, North Holland, Publishing Co., N.Y. 1978)). In a typical immunometric assay, a quantity of unlabeled antibody is bound to a solid support that is insoluble in the fluid being tested, e.g., blood, lymph, cellular extracts, etc. After the initial binding of antigen to immobilized antibody, a quantity of detectably labeled second antibody (which may or may not be the same as the first) is added to permit detection and/or quantitation of bound antigen (see e.g., Kirkham, et al., *Radioimmune Assay Method*, E&S Livingstone, Edinburgh, pp. 199-206 (1970)). Many variations of these types of assays are known in the art and may be employed for the detection of peptide.

Antibodies may also be used to purify peptide, (see generally, Dean, et al., *Affinity Chromatography, A Practical Approach*, IRL Press (1986)). Typically, antibody is immobilized on a chromatographic matrix such as Sepharose, 4B. The matrix is then packed into a column and the preparation containing peptide is passed through under conditions that promote binding, e.g., under conditions of low salt. The column is then washed and bound peptide is eluted using a buffer that promotes dissociation from antibody, e.g., buffer having an altered pH or salt concentration. The eluted peptide may be transferred into a buffer of choice and then stored or used directly.

D. Pharmaceutical Compositions and Methods of Treatment

The peptides described herein may be incorporated into a pharmaceutical composition and administered to patients to prevent reperfusion injuries associated with stroke, heart attack, or spinal injury. The peptides may also be given to patients prior to surgery in order to reduce cellular damage due to oxidative stress. The total dosage of peptide administered to a patient should be at least the amount required to produce a statistically significant reduction in oxidative damage. Although this will vary depending upon clinical conditions, it is expected that a typical daily dosage of peptide will be between 0.01 mg and 10 mg. High concentrations of peptide, e.g., 10 µM or more, may be continually infused at sites where oxidative damage may be expected to occur, e.g., at the location of a spinal injury or to cardiac tissue to prevent reperfusion damage after a heart attack. These dosages are simply guidelines as the actual dose selected for an individual patient will be determined by the attending physician based upon clinical conditions and using methods that are well known in the art.

Any route of administration and dosage form is compatible with the present invention and therapeutic peptides may be administered as either the sole active agent or in combination with other therapeutically active drugs. In general, parenteral delivery will be used in order to avoid potential inactivation in a patient's gastrointestinal tract. Routes of delivery compatible with the invention include continuous perfusion, peroral, internal, intrathecal, pulmonary, rectal, nasal, vaginal, lingual, transdermal, intravenous, intraarterial intramuscular, intraperitoneal, intracutaneous and subcutaneous administration. Specific dosage forms that may be used include tablets, pills, capsules, powders, aerosols, suppositories, skin patches, parenterals, and oral liquids, including aqueous suspensions, solutions, and emulsions. Sustained release dosage forms may also be used. All dosage forms may be prepared using methods that standard in the art (see e.g., *Remington's Pharmaceutical Sciences*, 16$^{th}$ ed., A. Oslo ed., Easton, Pa. (1980)).

Peptides may be used in conjunction with any of the vehicles and excipients commonly employed in pharmaceutical preparations, e.g., talc, gum arabic, lactose, starch, magnesium stearate, cocoa butter, aqueous or non-aqueous solvents, oils, paraffin derivatives, glycols, etc. Coloring and flavoring agents may also be added to preparations designed for oral administration. Solutions can be prepared using water or physiologically compatible organic solvents such as ethanol, 1,2-propylene glycol, polyglycols, dimethylsulfoxide, fatty alcohols, triglycerides, partial esters of glycerin and the like. Parenteral compositions containing peptide may be prepared using conventional techniques and include sterile isotonic saline, water, 1,3-butane diol, methanol, 1,2-propyleneglycol, polyglycols mixed with water, Ringer's solution, etc.

If desired, a patient can be initially given a relatively low dose of peptide in order to determine whether any adverse side-effects are experienced. This may be particularly important in cases where a patient is taking other medications or has clinical characteristics that suggest that they might not be able to tolerate high drug dosages. If adverse side effects are not experienced by a patient, dosage may be gradually increased.

EXAMPLES

Computer-based alignments of APP and H-ferritin were run using the Gap and Bestfit sequence alignment programs for Vax software. Using a ferrozine based assay (de Silva, et al., *J. Biol. Chem.* 272:14208–14213 (1997)), it was found that purified APP, like ferritin, displays catalytic ferroxidase activity. Using 6.5 nM of protein, the Vmax of iron oxidation for APP was found to be 0.5 µM/min. Ceruloplasmin (Cp) a known ferroxidase, exhibited a Vmax value of 5 µM/min. Bovine serum albumin (BSA) served as a negative control for these experiments since 6.5 µM BSA provided a 5-fold lower apparent rate of iron oxidation (an apparent reaction rate of 0.1 µM iron oxidized per minute). It was concluded that purified, secreted APP ectodomain specifically catalyzes the oxidation of 100-fold more iron per minute than the amount of APP present. This is an indication that APP harbors one or more sites for catalytic iron oxidation.

Using synthetic peptides, it was confirmed that sequences overlapping the newly identified FOX-1 domain in APP function as intrinsic ferroxidases. A peptide designated as "A2" (coding for residues 316 to 337 in APP-695)was tested. At concentrations equal to 0.5 µM, the A2 peptide specifically oxidizes iron at a rate significantly higher than BSA or RNase-A, another negative control protein. Using the ferroxine-based iron oxidation assay, the A2 peptide exhibited iron oxidase activity with a Vmax of 2.96 µM/min/ 0.5 µM peptide. RNase-A (0.5 µM) exhibited an apparent Vmax of 1.96 mM iron/min/0.5 µM peptide (n=6). Ceruloplasmin (Cp) was used as a positive control since Cp is a known copper-dependent iron oxidase. Cp specifically oxidized iron with a reaction velocity (Vmax) of 4.2 mM iron per min/0.5 µM protein n=6. The standard error for each of these reactions was less than 5%.

The known RERMS domain of APP (319 to 335 with respect to APP-695) is a cytoprotective region of APP and overlaps the A2 to peptide described above. However, another peptide tested, 827, encodes a completely new APP sequence (327–348) which aligns even more significantly with the cytoprotective H-ferritin ferroxidase site. The 827 sequence is HRBRMSQVMREWEEAERQAKNL (SEQ ID NO: 6), encoding 9 amino terminal amino acids that overlap with the RERMS peptide. In addition, 827 has 13 unique amino acids that align with the ferritin iron oxidase domain, as present in FOX-1. In another set of ferrozine-based assays, it was found that the 827 peptide has ferroxidase activity. Specifically, this set of experiments showed Vmax values of (i) 7.36 µM/min, (ii) 2.78 µM/min; (iii) 6.41 µM/min; and (iv) 1.05 µM/min for the rates of iron oxidation respectively from 0.5 µM each of (i) 827 peptide; (ii) the A2 peptide; (iii) Cp; and (iv) RNaseTI. It was concluded that peptides spanning sequences from 316 to 346 of APP-695 can be used as agents to protect cells from iron catalyzed cellular damage. It was also concluded that peptides exhibit higher oxidase activity as their homology with ferritin ferroxidase increases.

The experiments performed suggest that peptides designed from the FOX-1 domain of APP should provide cytoprotection from iron-catalyzed damage (including siderosis) for neuronal cells. The data support the use of peptides against iron catalyzed oxidative damage such as that resulting from a reperfusion/ischemic reaction in victims of stroke and spinal injury.

All references cited herein are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

What is claimed is:

1. A peptide comprising the amino acid sequence of SEQ ID NO:7, wherein said peptide has ferroxidase enzymatic activity.

2. A peptide with ferroxidase activity consisting essentially of the amino acid sequence of SEQ ID NO:7.

3. The peptide of either claim 2 or claim 1, wherein said peptide is substantially pure.

4. A pharmaceutical composition comprising a the peptide of either claim 2 or claim 1, together with a pharmaceutically acceptable carrier.

5. The pharmaceutical composition of claim 4, wherein said pharmaceutical composition is in unit dose form and comprises 0.01–10 mg of said peptide.

6. The pharmaceutical composition of claim 4, wherein said pharmaceutical composition is in the form of a liquid suitable for parenteral administration.

7. The pharmaceutical composition of claim 4, wherein said pharmaceutical composition is indicated for use in reducing oxidation-related damage in a patient suffering from stroke, heart attack, spinal injury or for administration to a patient undergoing surgery to reduce cellular injury resulting from oxidative stress.

8. A pharmaceutical composition in unit dose form comprising the peptide of either claim 2 or claim 1 together with a pharmaceutically acceptable carrier, wherein said peptide is present in a therapeutically effective amount for reducing oxidation-related damage in a patient suffering from stroke, heart attack, spinal injury, or for administration to a patient undergoing surgery to reduce cellular injury resulting from oxidative stress.

9. A peptide with ferroxidase activity consisting of the amino acid sequence of SEQ ID NO:7.

10. The peptide of claim 9, wherein said peptide is substantially pure.

11. A pharmaceutical composition comprising a the peptide of claim 4, together with a pharmaceutically acceptable carrier.

12. The pharmaceutical composition of claim 11, wherein said pharmaceutical composition is in unit dose form and comprises 0.01–10 mg of said peptide.

13. The pharmaceutical composition of either claim 11 or claim 12, wherein said pharmaceutical composition is in the form of a liquid suitable for parenteral administration.

14. The pharmaceutical composition of claim 13, wherein said pharmaceutical composition is indicated for use in reducing oxidation-related damage in a patient suffering from stroke, heart attack, spinal injury, or for administration to a patient before surgery to reduce cellular injury resulting from oxidative stress.

15. A pharmaceutical composition in unit dose form comprising the peptide of claim 9 together with a pharmaceutically acceptable carrier, wherein said peptide is present in a therapeutically effective amount for reducing oxidation-related damage in a patient suffering from stroke, heart attack, spinal injury, or for administration to a patient undergoing surgery to reduce cellular injury resulting from oxidative stress.

* * * * *

UNITED STATES PATENT AND TRADEMARK OFFICE
CERTIFICATE OF CORRECTION

| | |
|---|---|
| PATENT NO. | : 7,034,000 B2 |
| APPLICATION NO. | : 09/978178 |
| DATED | : April 25, 2006 |
| INVENTOR(S) | : Jack Rogers |

It is certified that error appears in the above-identified patent and that said Letters Patent is hereby corrected as shown below:

In column 1, lines 13-15, after "Statement of Government Support" should be corrected to specify the source of funding. The corrected paragraph should read as follows:

-- This invention was made with Government support under Grant No. AG016458 awarded by the National Institutes of Health. The U.S. Government therefore has certain rights in the invention. --

Signed and Sealed this

Eighteenth Day of August, 2009

David J. Kappos
*Director of the United States Patent and Trademark Office*

```
                        SEQUENCE LISTING

<160> NUMBER OF SEQ ID NOS: 7

<210> SEQ ID NO 1
<211> LENGTH: 10
<212> TYPE: PRT
<213> ORGANISM: Homo sapiens

<400> SEQUENCE: 1

Arg Glu Trp Glu Glu Ala Glu Arg Gln Ala
1               5                   10

<210> SEQ ID NO 2
<211> LENGTH: 14
<212> TYPE: PRT
<213> ORGANISM: Homo sapiens

<400> SEQUENCE: 2

Lys Asn Leu Pro Lys Ala Asp Lys Lys Ala Val Ile Gln His
1               5                   10

<210> SEQ ID NO 3
<211> LENGTH: 20
<212> TYPE: PRT
<213> ORGANISM: Homo sapiens

<400> SEQUENCE: 3

Phe Gln Lys Ala Lys Glu Arg Leu Glu Ala Lys His Arg Glu Arg Met
1               5                   10                  15

Ser Gln Val Met
            20

<210> SEQ ID NO 4
<211> LENGTH: 13
<212> TYPE: PRT
```

```
<213> ORGANISM: Homo sapiens

<400> SEQUENCE: 4

Arg Glu Trp Glu Glu Ala Glu Arg Gln Ala Lys Asn Leu
1               5                   10

<210> SEQ ID NO 5
<211> LENGTH: 24
<212> TYPE: PRT
<213> ORGANISM: Homo sapiens

<400> SEQUENCE: 5

Arg Glu Trp Glu Glu Ala Glu Arg Gln Ala Lys Asn Leu Pro Lys Ala
1               5                   10                  15

Asp Lys Ala Val Ile Gln His
            20

<210> SEQ ID NO 6
<211> LENGTH: 22
<212> TYPE: PRT
<213> ORGANISM: Homo sapiens

<400> SEQUENCE: 6

His Arg Glu Arg Met Ser Gln Val Met Arg Glu Trp Glu Glu Ala Glu
1               5                   10                  15

Arg Gln Ala Lys Asn Leu
            20

<210> SEQ ID NO 7
<211> LENGTH: 23
<212> TYPE: PRT
<213> ORGANISM: Homo sapiens

<400> SEQUENCE: 7

Asp Gly Asp Glu Val Glu Glu Glu Ala Glu Pro Tyr Glu Glu Ala Thr
1               5                   10                  15

Glu Arg Thr Thr Ser Ile Ala
            20
```